US00PP16263P2

(12) United States Plant Patent
Saul

(10) Patent No.: US PP16,263 P2
(45) Date of Patent: Feb. 14, 2006

(54) *ALTERNANTHERA* PLANT NAMED 'CREME DE MENTHE'

(50) Latin Name: *Alternanthera ficoidea*
Varietal Denomination: Creme de Menthe

(75) Inventor: Robert Mark Saul, Atlanta, GA (US)

(73) Assignee: Itsaul Plants, Alpharetta, GA (US)

( * ) Notice: Subject to any disclaimer, the term of this patent is extended or adjusted under 35 U.S.C. 154(b) by 47 days.

(21) Appl. No.: 11/022,001

(22) Filed: Dec. 24, 2004

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Alternanthera* plant named 'Creme de Menthe', characterized by its upright and columnar plant habit; freely basal branching habit; bushy and dense growth habit; and green and pale yellow bi-colored leaves.

1 Drawing Sheet

Botanical designation: *Alternanthera ficoidea.*
Cultivar denomination: 'Creme de Menthe'.

CROSS REFERENCE TO RELATED APPLICATIONS

The present application is co-pending with the following related applications:

*Alternanthera* Plant Named 'Cognac'.

*Alternanthera* Plant Named 'Grenadine'.

BACKGROUND OF THE INVENTION

The present Invention relates to a new and distinct cultivar of *Alternanthera* plant, botanically known as *Alternanthera ficoidea*, and hereinafter referred to by the name 'Creme de Menthe'.

The new *Alternanthera* was discovered in September, 2002, by the Inventor in a controlled environment in Chamblee, Ga., as a naturally-occurring branch mutation of the *Alternanthera ficoidea* cultivar Partytime, disclosed in U.S. Plant Pat. No. 14,789. The cultivar Creme de Menthe was selected by the Inventor on the basis of its unique foliage coloration.

Asexual reproduction of the new cultivar by vegetative cuttings in Chamblee, Ga. since October, 2002, has shown that the unique features of this new *Alternanthera* are stable and reproduced true to type in successive generations.

SUMMARY OF THE INVENTION

Plants of the cultivar Creme de Menthe have not been observed under all possible environmental conditions. The phenotype may vary somewhat with variations in environment such as temperature and light intensity without, however, any variance in genotype.

The following traits have been repeatedly observed and are determined to be the unique characteristics of 'Creme de Menthe'. These characteristics in combination distinguish 'Creme de Menthe' as a new and distinct cultivar:

1. Upright and columnar plant habit.
2. Freely basal branching habit; bushy and dense growth habit.
3. Green and pale yellow bi-colored leaves.

Plants of the new *Alternanthera* can be compared to plants of the parent, the cultivar Partytime. In side-by-side comparisons conducted in Chamblee, Ga., plants of the new *Alternanthera* differed from plants of the cultivar Partytime in the following characteristics:

1. Plants of the new *Alternanthera* were taller than plants of the cultivar Partytime.
2. Plants of the new *Alternanthera* had larger and glossier leaves than plants of the cultivar Partytime.
3. Plants of the new *Alternanthera* and the cultivar Partytime differed in foliage coloration as plants of the cultivar Partytime had green, creamy white and red purple-colored leaves.

Plants of the new *Alternanthera* can also be compared to plants of the cultivars Cognac, disclosed in U.S. Plant patent application Ser. No. 11/022,012, and Grenadine, disclosed in U.S. Plant patent application Ser. No. 11/022,000. In side-by-side comparisons conducted in Chamblee, Ga., plants of the new *Alternanthera* differed from plants of the cultivars Cognac and Grenadine primarily in leaf coloration as plants of the cultivar Cognac had dark purplish brown-colored leaves and plants of the cultivar Grenadine had brown and red purple bi-colored leaves.

BRIEF DESCRIPTION OF THE PHOTOGRAPH

The accompanying colored photograph illustrates the unique appearance of the new cultivar, showing the colors as true as it is reasonably possible to obtain in colored reproductions of this type. Colors in the photograph may differ from the color values cited in the detailed botanical description which accurately describe the colors of the new *Alternanthera*. The photograph is a top perspective view of a typical plants of 'Creme de Menthe' grown in a container.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photograph and in the following description were grown in Atlanta, Ga. during the summer in an outdoor nursery and under conditions which closely approximate commercial production conditions. During the production of the plants, day temperatures ranged from 80 to 90° F. and night temperatures ranged from 60 to 75° F. Plants were about four months old when the photograph and description were taken.

Botanical classification: *Alternanthera ficoidea* cultivar Creme de Menthe.

Parentage: Naturally-occurring branch mutation of the *Alternanthera ficoidea* cultivar Partytime, disclosed in U.S. Plant Pat. No. 14,789.

Propagation:

*Type cutting*.—By vegetative cuttings.

*Time to initiate roots, summer*.—About 5 days at 80 to 90° F.

*Time to initiate roots, winter*.—About 10 days at 65 to 80° F.

*Time to produce a rooted cutting or liner, summer*.—About 21 days at 80 to 90° F.

*Time to produce a rooted cutting or liner, winter*.—About 30 to 35 days at 65 to 80° F.

*Root description*.—Fine, fibrous; off-white in color.

*Rooting habit*.—Freely branching.

Plant description:

*Form/growth habit*.—Upright and columnar plant habit; vigorous.

*Plant height, soil level to top of plant plane*.—About 33 cm.

*Plant diameter or area of spread*.—About 23 cm.

*Branching habit*.—Freely basal branching, about six basal branches per plant; pinching enhances lateral branch formation; dense and bushy growth habit.

*Basal branches*.—Length: About 29 cm. Diameter: About 4 mm. Internode length: About 5.3 cm. Texture: Fine pubescence; longitudinally ridged. Strength: Strong, but flexible. Color: 146A overlain with 187B.

*Foliage description*.—Arrangement: Opposite, simple. Length: About 8.5 cm. Width: About 5.2 cm. Shape: Ovate. Apex: Acute to acuminate. Base: Obtuse. Margin: Entire. Texture, upper and lower surfaces: Slightly pubescent; slightly rugose. Venation pattern: Pinnate. Color: Developing foliage, upper surface: Irregular sectors of close to 147A and close to 9D. Developing foliage, lower surface: Irregular sectors of close to 147B and close to 11D. Fully expanded foliage, upper and lower surfaces: Irregular sectors of close to 147A and close to 9D. Venation, upper surface: More green than 147A and 9D. Venation, lower surface: Close to 144A and 9D. Petiole: Length: About 2.4 cm. Diameter: About 2.5 mm. Texture, upper and lower surfaces: Pubescent. Color, upper and lower surfaces: 146A overlain with 187A to 187B.

Flower description: Flower development has not been observed on plants of the new *Alternanthera*.

Disease/pest resistance: Under commercial production conditions, plants of the new *Alternanthera* have not been observed to be resistant to pathogens or pests common to *Alternanthera*.

Weather tolerance: Plants of the new *Alternanthera* have been shown to be tolerant to rain, wind and to temperatures ranging from 32 to more than 100° F.

It is claimed:

1. A new and distinct cultivar of *Alternanthera* plant named 'Creme de Menthe', as illustrated and described.

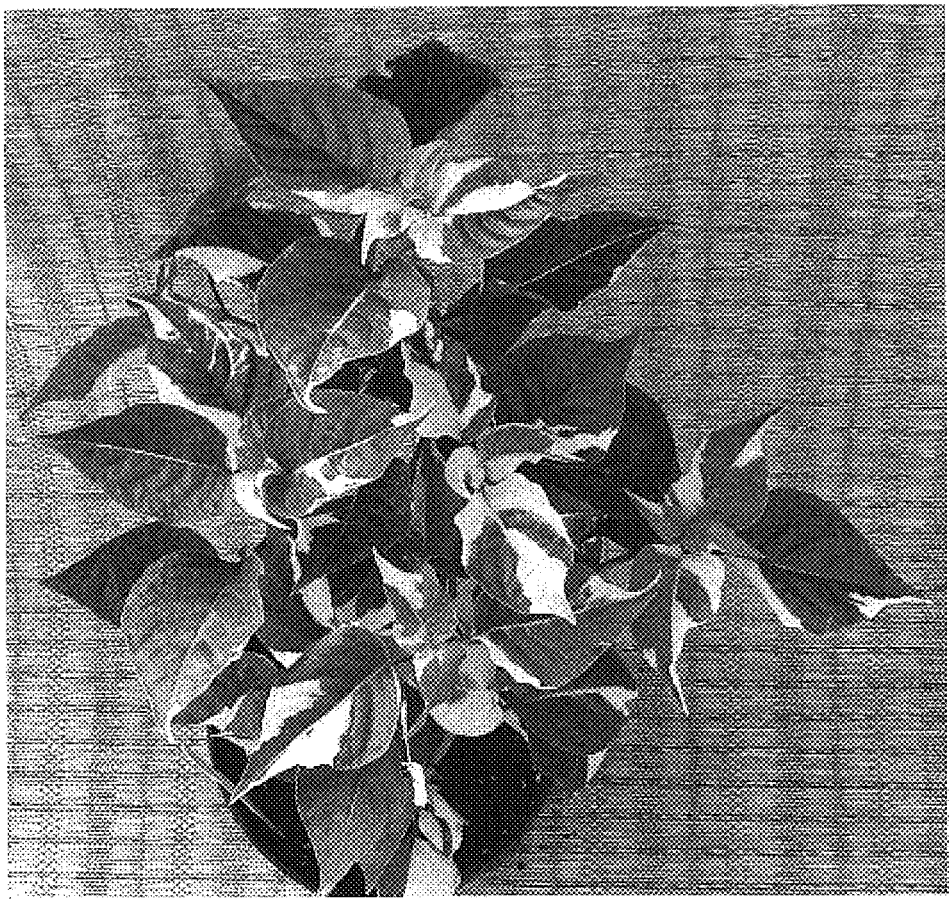

* * * * *